United States Patent [19]
Kang et al.

[11] Patent Number: 5,972,686
[45] Date of Patent: Oct. 26, 1999

[54] ICE NUCLEATION ACTIVE MICROORGANISM

[75] Inventors: Choong-Kyung Kang; Gwang-Hwee Na; Hyun-Geun Yoon; Seung-Suh Hong; Hyun-Soo Lee, all of Taejon, Rep. of Korea

[73] Assignee: Samyang Genex Co., Ltd., Seoul, Rep. of Korea

[21] Appl. No.: 09/077,218

[22] PCT Filed: Dec. 27, 1996

[86] PCT No.: PCT/KR96/00254

§ 371 Date: May 19, 1998

§ 102(e) Date: May 19, 1998

[87] PCT Pub. No.: WO98/12301

PCT Pub. Date: May 26, 1998

[30] Foreign Application Priority Data

Sep. 19, 1996 [KR] Rep. of Korea ................... 96-40870

[51] Int. Cl.$^6$ .................................................. C12N 1/20
[52] U.S. Cl. ..................... 435/252.1; 424/93.4; 426/61; 435/168; 435/262; 435/910
[58] Field of Search .................... 435/252.1, 168, 435/910, 262; 426/61; 424/93.4

[56] References Cited

U.S. PATENT DOCUMENTS

| 4,464,473 | 8/1984 | Orser et al. | 434/252.33 |
|---|---|---|---|
| 5,194,269 | 3/1993 | Lee | 426/61 |
| 5,489,521 | 2/1996 | So et al. | 435/168 |

OTHER PUBLICATIONS

Li. J. et al., Bacterial Ice Nucleation and Its Potential Application in the Food Industry, Trends in Food Science & Technology, 6:259–265(1995).

Watanabe M. et al., Screening, Isolation, and Identification of Food–originated Compounds Enhancing the Ice–nucleation Activity of *Xanthomonas Campestris*, Biosci. Biotech. Biochem., 58(1):64–66(1994).

Kawahara H. et al., Isolation and Characterization of a Novel Ice–nucleation Bacterium, Pseudomonas sp. KUIN–4 Which Has Stable Activity in Acidic Solution, Biosci. Biotech. Biochem., 59(8):1528–1532(1995).

Watanabe M. et al., Enhancing Effect of 4–Hydroxy–3–nitrophenylacetic Acid on Transcription of the Ice Nucleation–active Gene of *Xanthomonas campestris*, Biosci. Biotech. Biochem., 58(12):2269–2270(1994).

*Primary Examiner*—Herbert J. Lilling
*Attorney, Agent, or Firm*—Knobbe, Matens, Olson & Bear, LLP

[57] ABSTRACT

The present invention relates to a novel ice nucleation active Xanthomonas strain and a bacterial ice nucleator comprising the ice nucleation active microorganism which can be applied for food processing and artificial snow making. The present inventors have screened ice nucleation active microorganisms from leaves of crops and plants, and investigated their ice-nucleation activities. As a result, the inventors discovered that a novel microorganism belonging to *Xanthomonas campestris* has a superior ice-nucleation activity than those of the conventional ice nucleation active microorganisms. Accordingly, the ice nucleation active microorganism of the invention can be used as a potent bacterial ice nucleator for food processing and artificial snow making.

6 Claims, 2 Drawing Sheets

ICE NUCLEATION ACTIVE MICROORGANISM

BACKGROUND OF THE INVENTION

1. Field of the Invention

The present invention relates to a novel ice nucleation active microorganism, more specifically, to a novel ice nucleation active Xanthomonas strain and a bacterial ice nucleator comprising the ice nucleation active microorganism which can be applied for food processing and artificial snow making.

2. Description of the Prior Art

Microbial ice nucleation(the initiation of the crystallization of liquid water into solid ice) has been studied since the early 1970's, and it has been discovered that frost and cold-weather injuries in plants are caused by microorganism, not by climate effect(see: Schnell and Vali, Nature, 246(23):21–33(1973)). Also, studies on ice nucleation protein("INP") have followed, since the discovery that the damage is originated from the INP of ice nucleation active microorganism. Thus, it has been found that the INP has an ice-nucleation activity, and microorganisms producing the protein are ephiphytic microorganisms living on the surface of plant leaves.

Bacterial ice-nucleation activity have been researched, chiefly concentrated on the prevention of frost injury to the agricultural crops and its potential application in various technical areas. As a result, microbial strains competing with the ice nucleation active microorganisms or mutants losing the ice-nucleation activity have been developed to prevent frost injury caused by the ice nucleation active microorganisms(see: Lindemann and Suslow, Phytopathol., 77:882–886(1987)). In the application of the ice nucleation active microorganism, it has been widely used as an inducer for artificial snow making.

Though it has been known that water freezes at 0° C., the probability that pure water will nucleate homogenously at 0° C. is, in fact, zero. As tiny droplets of pure water(less than 1 μm in diameter) are decreased in temperature, the probability approaches 1 at −41° C. A temperature of −41° C. is usually accented as the limit to which water can be super-cooled. However, the freezing of water is catalyzed at −2° C. to −4° C. in the presence of INP, since the INP elevates the freezing point of water. In general, several ice nucleation active bacteria are able to catalyze ice formation at temperature as warm as −2° C. That is, though the freezing of water requires super-cooling condition at −41° C., in the presence of INP, super-cooling condition at −2° C. to −4° C. is required, which results in the saving of energy.

The effect of energy saving enables the ice nucleation active microorganism to be industrially applied as a freeze-inducer for preserving food products. Accordingly, the ice nucleation active microorganism can contribute to the preservation of frozen foods, the production of ices, the prevention of loss, the improvement of quality and the saving of energy. Also, the ice nucleation active microorganism can be applied to the freeze-concentration of liquid food and the production of frozen food. In addition, the ice nucleation active microorganism can induce artificial rain during a drought as a stimulant of the artificial rain, and is presently tested for field. In conclusion, it is expected that the ice nucleation active microorganism can be applied to all industrial areas associated with ice nucleation active process.

Particularly, the application of bacterial ice nucleator reduces freezing times and improves the quality of frozen foods, which suggests that there may be profound potential for quality improvement in food industry. Application of ice nucleation active microorganism in food industry has following advantages: First, energy required for freezing of food products is remarkably saved, since freezing occurs at −5° C. or more employing ice nucleation active microorganism while the conventional freeze-concentration or freeze-drying processes require a cooling temperature of −20 to −30° C. Since the freeze-concentration requires much energy for cooling, it has not practically been used regardless of its distinguished merits. However, the use of ice nucleation active microorganism permits wide use of freeze-concentration or freeze-drying due to the effect of energy saving. Secondly, the use of ice nucleation active microorganism in food processing leads to development of goods having a new property. For example, ice nucleation active microorganisms encapsulated in alginate gel, are used for freeze-drying of soy sauce and soybean paste, which makes possible energy saving caused by rapid freezing and easy grinding caused by porous dried structure. Also, through freeze-texturing of egg albumin, etc. employing ice nucleation active microorganism, texture of specific flake shape can be obtained, which has a distinction over the texture conventionally obtained by freeze-texturing. Furthermore, it has been reported that gel made of egg albumin which is freeze-concentrated by the aid of ice nucleation active microorganism has good properties of matter in light of foam formation and stability (see: Michiko, W. et al., J. food Eng., 22:453–473 (1994); Keiko, K. et al., Biol. Biotech. Biochem., 57(5):750–752(1993)).

Besides, studies on the production of foods of high quality by a combined use of ice nucleation active microorganism and ultra-high pressure processing, have been actively carried out. For example, freeze-concentrated milk whose protein components are not denaturated by heat treatment, by employing ice nucleation active microorganism, have been found to form specified gel during pressurization although gelling agent is not added therein. Since the gel thus formed has good color, good brightness and fresh cream-flavor, a dessert of high quality have been made of the gel(see: Rikimaru, H. et al., Agri. Biol. Chem., 53(11) :2935–2939 (1989)). Also, strawberry jam having good natural flavor and containing much vitamin C can be produced, compared to the conventional strawberry jam made by heat treatment, when strawberry paste was freeze-concentrated using ice nucleation active microorganism and then pressurized(see: Michiko, W. et al., Agri. Biol. Chem., 55(8):2175–2176 (1991)).

On the other hand, ice nucleation active microorganisms have been applied, primarily concentrated on the bacterial strains of Pseudomonas and Erwinia species, in the technical areas covering freeze-drying process, commercially important ice or snow making, and food processing employing the said microorganisms. However, the use of ice nucleation active microorganism belonging to Pseudomonas or Erwinia species can not guarantee safety of food products, and ice-nucleation activity of the said microorganisms has to be improved so that they can be applied as bacterial ice nucleator for food processing.

Accordingly, there are strong reasons for exploring and developing alternative ice nucleation active microorganism, to solve the problems of conventional strains in light of ice-nucleation activity and safety of this particular material in the commercial freezing of food products.

SUMMARY OF THE INVENTION

The present inventors have made an effort to develop a novel ice nucleation active microorganism for its potential application in the food industry and artificial snow making. That is, they have screened ice nucleation active microorganisms from leaves of crops and plants, and investigated their ice-nucleation activities. As a result, the inventors discovered that a novel microorganism belonging to Xanthomonas species has a superior ice-nucleation activity than the conventional ice nucleation active microorganisms.

A primary object of the invention is, therefore, to provide a novel ice nucleation active microorganism.

The other object of the invention is to provide a bacterial ice nucleator comprising the microorganism for food processing and artificial snow making.

BRIEF DESCRIPTION OF THE DRAWINGS

The above and the other objects and features of the present invention will become apparent from the following descriptions given in conjunction with the accompanying drawings, in which.

DETAILED DESCRIPTION OF THE INVENTION

Figure 1:
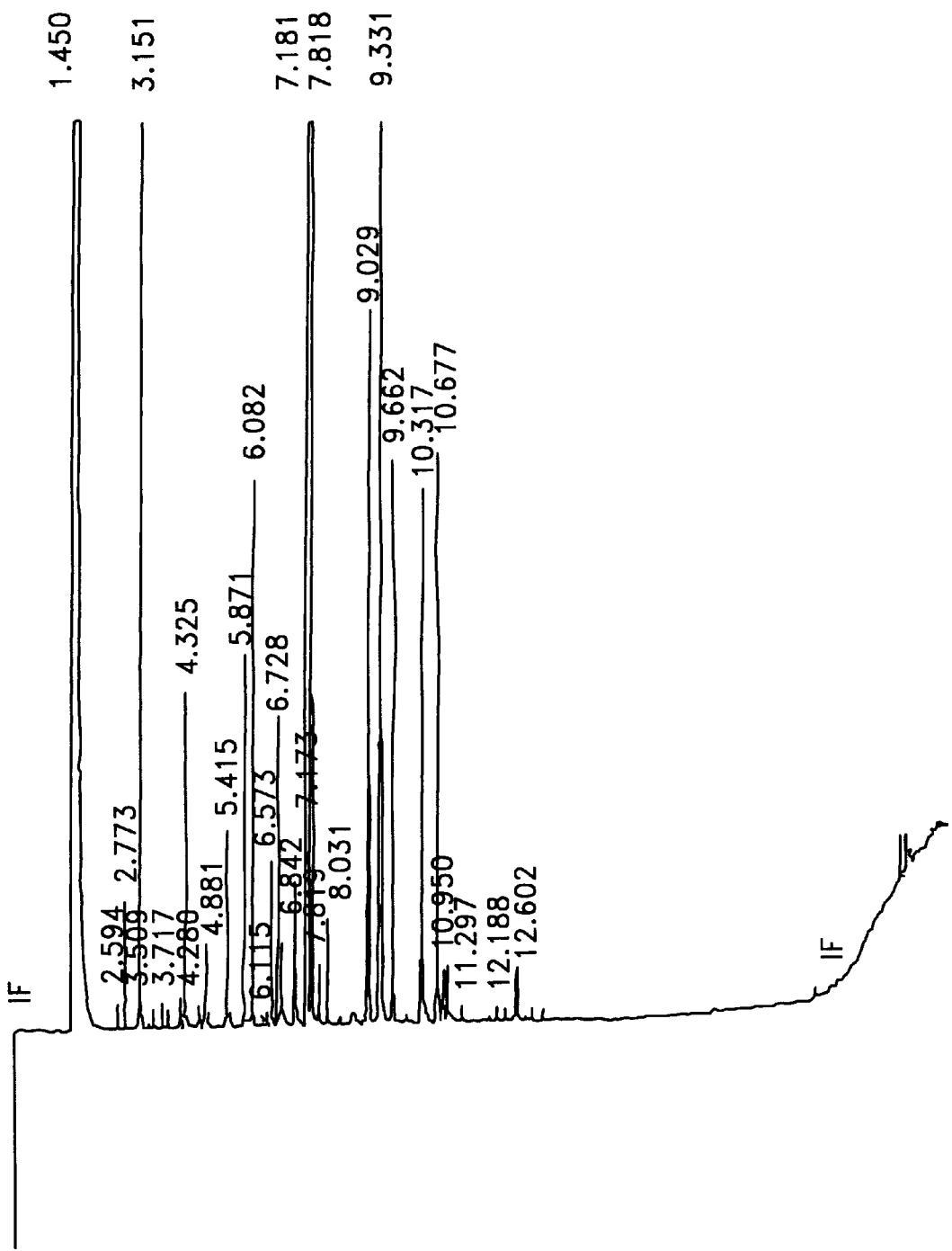
FIG. 1 is a gas chromatogram showing the result of fatty acid composition analysis of a novel ice nucleation active Xanthomonas strain of the present invention.

The present inventors have screened ice nucleation active microorganisms from leaves of crops and plants collected in Cheju Island and Cheollanam-Do in Korea, and 4 strains showing high activities were finally selected. Then, general characteriation was carried out for the identification of the microorganisms, while analyzing their fatty acid compositions of cell membranes. As a result, it has been found that a strain showing the highest ice-nucleation activity is a novel ice nucleation active microorganism belonging to *Xanthomonas campestris*. Therefore, the said microorganism designated as *Xanthomonas campestris* SYG 56-1, and was deposited with the Korean Collection for Type Cultures (KCTC) affiliated to the Korea Research Institute of Bioscience and Biotechnology(KRIBB), an international depositary authority as deposition No. KCTC 0251BP on Jun. 21, 1996.

Ice-nucleation activity of the microorganism was compared with the conventional ice nucleation active microorganisms. As a result, it has been found that ice-nucleation activity of *Xanthomonas campestris* SYG 56-1 of the invention is much higher than those of the commercially available Snomax™, *Pseudomonas syringae* and *Xanthomonas campestris* INXC-1. Moreover, the ice nucleation active microorganism of the invention was revealed to be widely used as a microbial agent for food processing, since the microorganisms belonging to *Xanthomonas campestris* have been applied for the production of Xanthan gum, which is a basic material for food processing, and whose safety is fully guaranteed.

The present invention is further illustrated in the following examples, which should not be taken to limit the scope of the invention.

EXAMPLE 1
Screening and identification of ice nucleation active microorganism The present inventors screened ice nucleation active microorganisms from leaves of crops and plants collected in Cheju Island and Cheollanam-Do in Korea. Samples were collected and suspended in a sterilized 10 mM phosphate buffer(pH 7.0), and their ice-nucleation activities were determined at the temperatures of $-3.0°$ C. and $-4.5°$ C., respectively. As a result, samples showing higher activities were plated on NA solid media(glycerol 2.5%, bacto-peptone 3.3 g/l, yeast extract 2.0 g/l, nutrient broth 2.7 g/l) and cultured at 25° C. Then, colonies thus obtained were cultured in NA liquid media, and their ice-nucleation activities were determined according to Vali's drop-freezing method described in Example 2 below. As a result, 4 strains showing high activities were selected and a strain showing the highest ice-nucleation activity was finally isolated. Then, microbial identification of the strain followed, by comparing them with the strains disclosed in Bergy's Manual (see: Table 1). As can be seen in Table 1 showing general characteristics of the isolated strain, it was revealed that the bacterial strain of the invention is a novel ice nucleation active microorganism belonging to Xanthomonas species. Also, analysis of fatty acid composition of cell membrane was carried out employing a MIDI Dos System(Hewlett Packard 5890 Series II MIS, USA), which revealed that the strain is a novel one having a similar fatty acid composition of *Xanthomonas campestris*. Therefore, the said microorganism designated as *Xanthomonas camsestris* SYG 56-1, and was deposited with the Korean Collection for Type Cultures(KCTC) affiliated to the Korea Research Institute of Bioscience and Biotechnology(KRIBB), an international depositary authority as deposition No. KCTC 0251BP on Jun. 21, 1996.

TABLE 1

| Characteristics | Morphology, physiology and biochemistry of *Xanthomonas campestris* SYG 56-1 | | |
|---|---|---|---|
| | *Xanthomonas campestris* SYG 56-1 | *Xanthomonas campestris*[*] | |
| Gram stain | — | — | |
| Shape | Rods | Rods | |
| Aerobic growth | + | + | |
| Motility | + | + | |
| Mucoid growth on nutrient agar + 5% glucose | + | + | + |
| Xanthmonadin produced | + | | |
| Growth on nutrient agar | + | + | |
| Growth rate moderate | + | + | |
| Hydrolysis of gelatin | + | d | |
| Urease activity | — | — | |
| Utilization of glucose | + | + | |
| Utilization of arabinose | + | + | |
| Utilization of fnannose | + | + | |
| Utilzation of mannitol | + | — | |
| Utilization of sucrose | + | + | |
| Utilization of matate | + | + | |
| Reduction of nitrates | — | — | |
| Reduction of nitrogen | — | — | |
| Indol production | — | — | |

[*] Bergy's Manual of Determinative Bacteriology, 2nd ed., The Williams & Wilkins Co., Baltimore, USA

EXAMPLE 2
Measurement of ice-nucleation activity

The ice nucleation active microorganism was batch-cultured in a medium disclosed in Table 2 for 30 hours at a temperature of 22° C.

TABLE 2

| Medium for the culture of ice nucleation active microorganism of the invention | |
|---|---|
| Components | Composition |
| Glycerol | 20 to 60 g/l |
| Yeast extract | 2 to 6 g/l |
| $(NH_4)_2SO_4$ | 0.5 to 2.0 g/l |
| $MgSO_4$•$7H_2O$ | 0.5 g/l |
| $KH_2PO_4$ | 0.35 g/l |
| $CaCl_2$•$2H_2O$ | 22 mg/l |
| $FeSO_4$•$7H_2O$ | 14 mg/l |

Ice-nucleation activity was determined according to Vali's drop-freezing method(see: Schnell, R. C. and G. Vali, Nature, 236:163–165(1972)). That is, the test microorganisms cultured in the said media, were resuspended in 10 mM phosphate buffer(pH 7.0) in a density of $3\times10^9$ cells/ml, and diluted by serial tenfold-dilution with 10 mM phosphate buffer(pH 7.0). 5 $\mu$l of the diluted solutions were aliquoted on the aluminum blocks coated with paraffin, which were transferred to the refrigerated batch circulater(JEIO-TECH, Korea).while incubating with a constant cooling rate from 0° C. to −10° C. Then, frozen drops according to super-cooling temperature were counted, and ice-nucleation activity was determined according to the following equation:

$$CNI=-Ln(1-f)/(V\times D)$$

wherein,

CNI, f, V and D are cumulated number of ice, ratio of frozen drops, volume(ml) of a drop and dilution fold, respectively.

EXAMPLE 3

Figure 2:
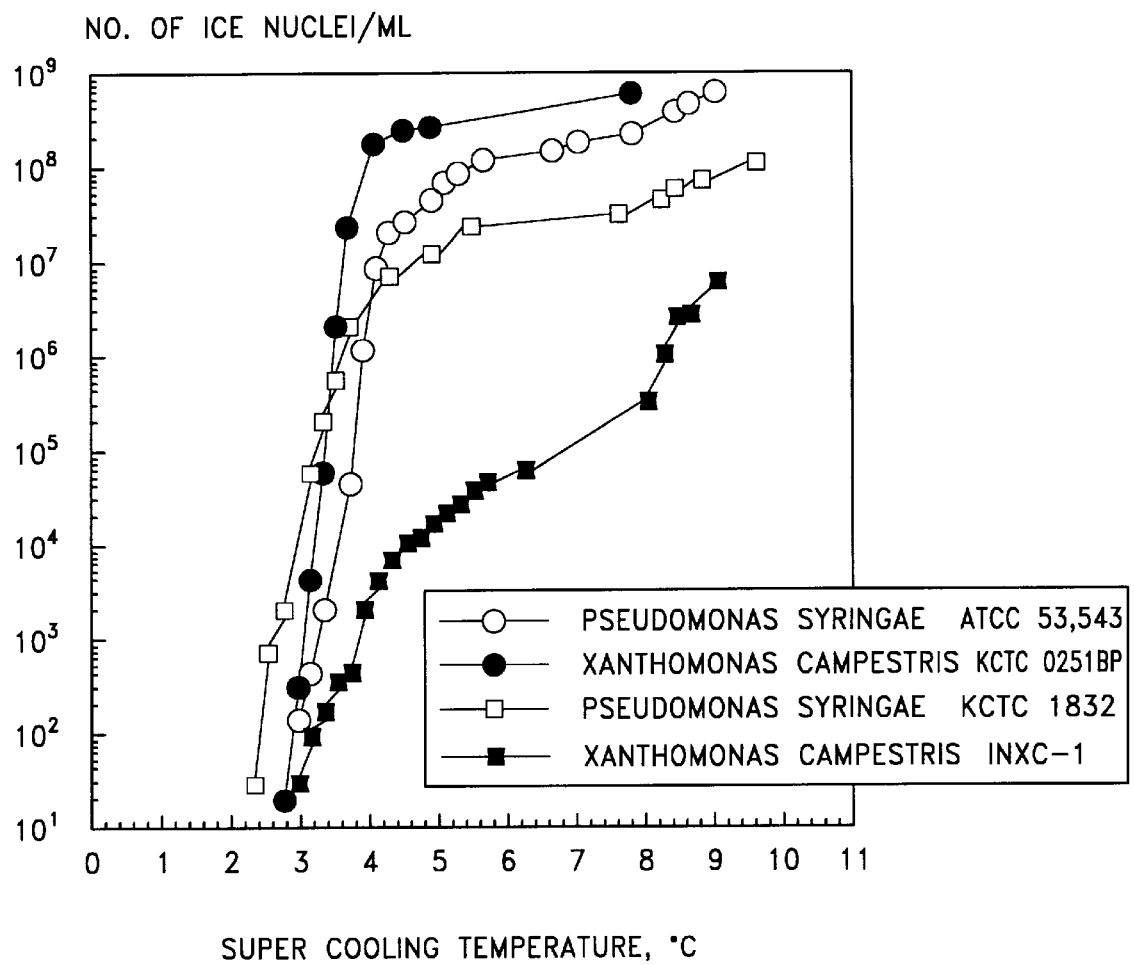
FIG. 2 is a graph showing ice-nucleation activities of the ice nucleation active microorganism of the invention and conventional ice nucleation active microorganisms.

Ice-nucleation activity of the ice nucleation active microorganism of the invention Ice-nucleation activity of the ice nucleation active microorganism of the invention was determined and compared with those of the commercial and the conventional ice nucleation active microorganism. That is, *Pseudomonas syringae* (ATCC 53543) from Snomax™ (Genencor, USA) which is a commercial ice nucleating agent, *Xanthomonas campestris* SYG 56-1 (KCTC 0251BP) which is an ice nucleation active microorganism of the invention, *Pseudomonas syringae* (KCTC 1832) and *Xanthomonas campestris* INXC-1 which are the conventional ice nucleation active microorganisms, were cultured in the above media for 30 hours at 22° C., respectively. Then, the cells were freeze-dried, and resuspended in a density of $10^9$ cells/ml in 10 mm phosphate buffer(pH 7.0), and diluted to $10^7$-fold by serial tenfold-dilution. 5 $\mu$l of the diluted solutions were aliquoted on the aluminum blocks, which were incubated with a constant cooling rate of 0.6° C./min from 0° C. to −10° C. Then, frozen drops according to super-cooling temperature were counted, and cumulated number of ice(CNI) was calculated according to the equation described in Example 2. FIG. 2 shows correlation of the calculated CNI with super-cooling temperature. In FIG. 2, (-○-), (-●-), (-□-) and (-■-) indicate ice-nucleation activities of *Pseudomonas syringae* (ATCC 53543) from Snomax™, *Xanthomonas campestris* SYG 56-1 (KCTC0251BP), *Pseudomonas syringae* (KCTC 132), and *Xanthomonas campestris* INXC-1, respectively. As shown in FIG. 2, it was found that ice-nucleation activity of *Xanthomonas campestris* SYG 56-1 of the invention is much higher than those of the commercially available Snomax™, *Pseudomonas syringae* and *Xanthomonas campestris* INXC-1.

As clearly illustrated and demonstrated as aboves, the present invention provides a novel ice nucleation active microorganism which has much higher ice-nucleation activity than those of the conventional ice nucleation active microorganisms. The ice nucleation active microorganism of the invention can be used as a potent bacterial ice nucleator for food processing and artificial snow making.

What is claimed is:

1. *Xanthomonas campestris.*

2. A bacterial ice nucleator which comprises *Xanthomonas campestris* KCTC 0251BP, and an appropriate carrier.

3. The bacterial ice nucleator of claim 2 wherein the carrier is suitable for food processing.

4. The bacterial ice nucleator of claim 2 wherein the carrier is suitable for artificial snow making.

5. A method for forming ice nuclei, comprising the steps of:

contacting a subject containing liquid water with *Xanthomonas campestris* KCTC 0251BP; and bacterially forming ice nuclei from the liquid water in the subject at super-cooling temperatures.

6. The method according to claim 5, wherein the super-cooling temperature is in the range of −2° to −4° C.

* * * * *